(12) United States Patent
Lane et al.

(10) Patent No.: US 9,309,204 B2
(45) Date of Patent: Apr. 12, 2016

(54) PROCESS FOR MAKING HYDROXYLATED CYCLOPENTYLPYRIMIDINE COMPOUNDS

(71) Applicants: Array BioPharma Inc., Boulder, CO (US); Genentech, Inc., South San Francisco, CA (US)

(72) Inventors: Jonathan W. Lane, Boulder, CO (US); Travis Remarchuk, South San Francisco, CA (US); Sagar Shakya, Boulder, CO (US); Keith L. Spencer, Boulder, CO (US); Peter J. Stengel, Boulder, CO (US)

(73) Assignees: ARRAY BIOPHARMA INC., Boulder, CO (US); GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/401,091

(22) PCT Filed: May 17, 2013

(86) PCT No.: PCT/US2013/041624
§ 371 (c)(1),
(2) Date: Nov. 13, 2014

(87) PCT Pub. No.: WO2013/173736
PCT Pub. Date: Nov. 21, 2013

(65) Prior Publication Data
US 2015/0099881 A1 Apr. 9, 2015

Related U.S. Application Data

(60) Provisional application No. 61/785,281, filed on Mar. 14, 2013, provisional application No. 61/648,421, filed on May 17, 2012.

(51) Int. Cl.
C07D 403/04 (2006.01)
C07D 239/70 (2006.01)
C07D 239/42 (2006.01)

(52) U.S. Cl.
CPC ............ *C07D 239/70* (2013.01); *C07D 239/42* (2013.01); *C07D 403/04* (2013.01)

(58) Field of Classification Search
CPC ... C07D 239/42; C07D 239/70; C07D 403/03
USPC .................................. 544/253, 295
See application file for complete search history.

(56) References Cited

U.S. PATENT DOCUMENTS

| 7,169,928 | B2 | 1/2007 | Schwartz et al. |
| 8,063,050 | B2 | 11/2011 | Mitchell et al. |
| 8,969,051 | B2 | 3/2015 | Hirata et al. |
| 2005/0130954 | A1 | 6/2005 | Mitchell et al. |
| 2008/0051399 | A1 | 2/2008 | Mitchell et al. |
| 2011/0281844 | A1 | 11/2011 | Schwartz et al. |
| 2012/0149684 | A1 | 6/2012 | Beight et al. |
| 2014/0121193 | A1 | 5/2014 | Katz et al. |
| 2015/0099880 | A1 | 4/2015 | Babu et al. |
| 2015/0148559 | A1 | 5/2015 | Remarchuk et al. |
| 2015/0152067 | A1 | 6/2015 | Askin et al. |
| 2015/0218602 | A1 | 8/2015 | Hirata et al. |

FOREIGN PATENT DOCUMENTS

| CN | 101918373 A | 12/2010 |
| CN | 101932564 A | 12/2010 |
| EP | 1188754 A1 | 3/2002 |
| WO | WO 95/15684 | 6/1995 |
| WO | WO 98/44797 | 10/1998 |
| WO | WO 98/56234 | 12/1998 |
| WO | WO 00/52134 | 9/2000 |
| WO | WO 01/22963 | 4/2001 |
| WO | WO 2004/108673 | 12/2004 |
| WO | WO 2008/006040 A1 | 1/2008 |
| WO | WO 2009/047255 | 4/2009 |
| WO | WO 2010/120935 | 10/2010 |
| WO | WO 2012/009649 | 1/2012 |
| WO | WO 2012/040258 | 3/2012 |
| WO | WO 2012/177925 | 12/2012 |
| WO | WO 2014/127350 | 8/2014 |
| WO | WO 2014/150395 | 9/2014 |

OTHER PUBLICATIONS

Patent Cooperation Treaty, International Searching Authority, Search Report and Written Opinion for PCT/US2013/041624, 9 pages, Jul. 3, 2013.

Lane, et al., "Route Scouting and Early Process Development of a Challenging Cyclopentylpyrimidine Intermediate in ARRY-4521GDC-0068", Organic Reactions and Processes, Gordon Research Conference, Poster, 1 page, Jul. 18, 2012.

*Primary Examiner* — Deepak Rao
(74) *Attorney, Agent, or Firm* — Viksnins Harris & Padys PLLP

(57) ABSTRACT

The invention provides new processes for making and purifying hydroxylated cyclopenta[d]pyrimidine compounds, which are useful for the treatment of diseases such as cancer as AKT protein kinase inhibitors, including the compound (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one.

16 Claims, No Drawings

PROCESS FOR MAKING HYDROXYLATED CYCLOPENTYLPYRIMIDINE COMPOUNDS

PRIORITY OF INVENTION

This application claims priority to U.S. Provisional Application No. 61/648,421 that was filed on 17 May 2012 and U.S. Provisional Application No. 61/785,281 that was filed on 14 Mar. 2013. The entire content of these provisional applications are hereby incorporated herein by reference.

FIELD OF THE INVENTION

Disclosed herein are processes for making and purifying cyclopentylpyrimidine compounds with therapeutic activity, against diseases such as cancer, as inhibitors of AKT kinase activity.

BACKGROUND OF THE INVENTION

The Protein Kinase B/Akt enzymes are a group of serine/threonine kinases that are overexpressed in certain human tumors. International Patent Application Publication Number WO 2008/006040 and U.S. Pat. No. 8,063,050 discuss a number of inhibitors of AKT, including the compound (S)-2-(4-chlorophenyl)-1-(4-4-((5R,7R)-7-hydroxy-5-methyl-6,7-dihydro-5H-cyclopenta[d]pyrimidin-4-yl)piperazin-1-yl)-3-(isopropylamino)propan-1-one (GDC-0068).

While processes described in WO 2008/006040 and U.S. Pat. No. 8,063,050 are useful in providing hydroxylated cyclopenta[d]pyrimidine compounds as AKT protein kinase inhibitors, alternative or improved processes are needed, including for large scale manufacturing of these compounds.

BRIEF SUMMARY OF THE INVENTION

Disclosed are processes for preparing, separating and purifying compounds detailed herein. Compounds provided herein include AKT protein kinase inhibitors, salts thereof, and intermediates useful in the preparation of such compounds.

One aspect includes a process comprising, contacting a compound of formula IV, or a salt thereof:

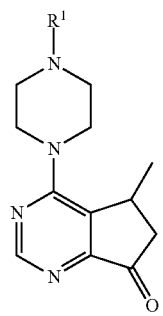

IV wherein:
$R^1$ is hydrogen or an amino protecting group;
$R^2$ is hydrogen or optionally substituted $C_1$-$C_{12}$ alkyl; and
$R^3$ is halogen,
with carbon monoxide, carbonylation catalyst and alcohol of formula $R^4OH$ to form a compound of formula III, or a salt thereof:

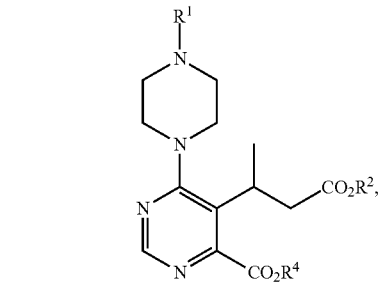

III wherein
$R^4$ is $C_1$-$C_6$ alkyl.

Another aspect includes a process comprising (i) reacting a compound of formula III, or salt thereof, with base to form an intermediate; and (ii) decarboxylating the intermediate to produce a compound of formula II, or a salt thereof.

II wherein $R^1$ is as defined for formula IV.

Another aspect includes a process comprising reducing a compound of formula II, or a salt thereof, to form a compound of formula I, or salt thereof

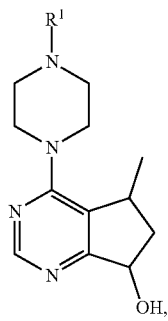

I wherein $R^1$ is as defined for formula IV.

Another aspect includes a process of preparing a compound of formula X or a salt thereof

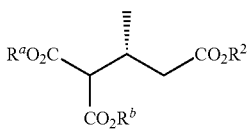

wherein $R^a$ and $R^b$ are independently $C_{1-12}$ alkyl; and $R^2$ is hydrogen or optionally substituted $C_1$-$C_{12}$ alkyl, the process comprising contacting a compound of formula XI with a lipase to form the compound of formula X

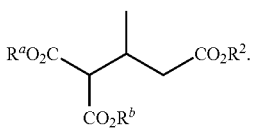

Another aspect includes a process of reacting a compound of formula X, or a salt thereof, with formamidine to form a compound of formula XII or a salt thereof,

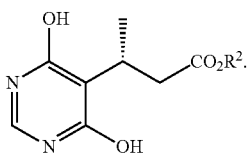

Another aspect includes a process comprising chlorinating a compound of formula XII or a salt thereof to form a compound of formula XIII.

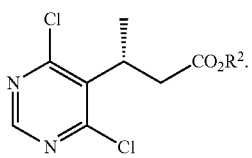

Another aspect includes a processes comprising contacting a compound of formula XIII or a salt thereof, with a compound

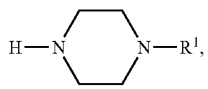

to form a compound of formula IVa or salt thereof.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. In the event that one or more of the incorporated literature and similar materials differs from or contradicts this application, including but not limited to defined terms, term usage, described techniques, or the like, this application controls.

"Acyl" means a carbonyl containing substituent represented by the formula —C(O)—R in which R is hydrogen, alkyl, a cycloalkyl, a heterocyclyl, cycloalkyl-substituted alkyl or heterocyclyl-substituted alkyl wherein the alkyl, alkoxy, cycloalkyl and heterocyclyl are independently optionally substituted and as defined herein. Acyl groups include alkanoyl (e.g., acetyl), aroyl (e.g., benzoyl), and heteroaroyl (e.g., pyridinoyl).

The term "alkyl" as used herein refers to a saturated linear or branched-chain monovalent hydrocarbon radical of one to twelve carbon atoms, and in another embodiment one to six carbon atoms, wherein the alkyl radical may be optionally substituted independently with one or more substituents described herein. Examples of alkyl groups include, but are not limited to, methyl(Me, —$CH_3$), ethyl(Et, —$CH_2CH_3$), 1-propyl(n-Pr, n-propyl, —$CH_2CH_2CH_3$), 2-propyl(i-Pr, i-propyl, —$CH(CH_3)_2$), 1-butyl(n-Bu, n-butyl, —$CH_2CH_2CH_2CH_3$), 2-methyl-1-propyl(i-Bu, i-butyl, —$CH_2CH(CH_3)_2$), 2-butyl(s-Bu, s-butyl, —$CH(CH_3)CH_2CH_3$), 2-methyl-2-propyl(t-Bu, t-butyl, —$C(CH_3)_3$), 1-pentyl(n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl(—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl(—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a linear or branched saturated divalent hydrocarbon radical of one to twelve carbon atoms, and in another embodiment one to six carbon atoms, wherein the alkylene radical may be optionally substituted independently with one or more substituents described herein. Examples include, but are not limited to, methylene, ethylene, propylene, 2-methylpropylene, pentylene, and the like.

The term "alkenyl" as used herein refers to a linear or branched-chain monovalent hydrocarbon radical of two to twelve carbon atoms, and in another embodiment two to six carbon atoms, with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), 1-propenyl, 1-buten-1-yl, 1-buten-2-yl, and the like.

The term "alkynyl" as used herein refers to a linear or branched monovalent hydrocarbon radical of two to twelve carbon atoms, and in another embodiment two to six carbon atoms, with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —CH₂C≡CH).

The term "alkoxy" refers to a linear or branched monovalent radical represented by the formula —OR in which R is alkyl, alkenyl, alkynyl or cycloalkyl, which can be further optionally substituted as defined herein. Alkoxy groups include methoxy, ethoxy, propoxy, isopropoxy, mono-, di- and tri-fluoromethoxy and cyclopropoxy.

"Amino" means primary (i.e., —NH₂), secondary (i.e., —NRH), tertiary (i.e., —NRR) and quaternary (i.e., —N⁺RRRX⁻) amines, that are optionally substituted, in which R is independently alkyl, alkoxy, a cycloalkyl, a heterocyclyl, cycloalkyl-substituted alkyl or heterocyclyl-substituted alkyl wherein the alkyl, alkoxy, cycloalkyl and heterocyclyl are as defined herein Particular secondary and tertiary amines are alkylamine, dialkylamine, arylamine, diarylamine, aralkylamine and diaralkylamine wherein the alkyls and aryls are as herein defined and independently optionally substituted. Particular secondary and tertiary amines are methylamine, ethylamine, propylamine, isopropylamine, phenylamine, benzylamine dimethylamine, diethylamine, dipropylamine and diisopropylamine.

The terms "cycloalkyl," "carbocycle," "carbocyclyl" and "carbocyclic ring" as used herein are used interchangeably and refer to saturated or partially unsaturated cyclic hydrocarbon radical having from three to twelve carbon atoms, and in another embodiment three to eight carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl ring fused to a saturated, partially unsaturated or aromatic cycloalkyl or heterocyclic ring. Examples of cycloalkyl groups include, but are not limited to, cyclopropyl, cyclobutyl, cyclopentyl, cyclohexyl, cycloheptyl, cyclohexenyl, cyclohexadienyl, cycloheptenyl and the like. Bicyclic carbocycles include those having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, and bicyclo[3.2.2]nonane. The cycloalkyl may be optionally substituted independently with one or more substituents described herein.

The term "aryl" as used herein means a monovalent aromatic hydrocarbon radical of 6-20 carbon atoms derived by the removal of one hydrogen from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "hetercyclyl" and "heterocyclic ring" as used herein are used interchangeably and refer to a saturated or partially unsaturated carbocyclic radical of 3 to 12 ring atoms in which at least one ring atom is a heteroatom independently selected from nitrogen, oxygen and sulfur, the remaining ring atoms being C, where one or more ring atoms may be optionally substituted independently with one or more substituents described below. One embodiment includes heterocycles of 3 to 7 membered ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabiclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1,1-dioxo-thiomorpholinyl. The heterocycle groups herein are optionally substituted independently with one or more substituents described herein.

The term "heteroaryl" as used herein refers to a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein.

"Amino-protecting group" as used herein refers to groups commonly employed to keep amino groups from reacting during reactions carried out on other functional groups. Examples of such protecting groups include carbamates, amides, alkyl and aryl groups, imines, as well as many N-heteroatom derivatives which can be removed to regenerate the desired amine group. Particular amino protecting groups are Ac (acetyl), trifluororacetyl, phthalimide, Bn (benzyl), Tr (triphenylmethyl or trityl), benzylidenyl, p-toluenesulfonyl, Pmb (p-methoxybenzyl), Boc (tert-butyloxycarbonyl), Fmoc (9-fluorenylmethyloxycarbonyl) and Cbz (carbobenzyloxy). Further examples of these groups are found in: Wuts, P. G. M. and Greene, T. W. (2006) Frontmatter, in Greene's Protective Groups in Organic Synthesis, Fourth Edition, John Wiley & Sons, Inc., Hoboken, N.J., USA. The term "protected amino" refers to an amino group substituted with one of the above amino-protecting groups.

The term "substituted" as used herein means any of the above groups (e.g., alkyl, alkylene, alkenyl, alkynyl, cycloalkyl, aryl, heterocyclyl and heteroaryl) wherein at least one hydrogen atom is replaced with a substituent. In the case of an oxo substituent ("=O") two hydrogen atoms are replaced. "Substituents" within the context of this invention include, but are not limited to, halogen, hydroxy, oxo, cyano, nitro, amino, alkylamino, dialkylamino, alkyl, alkenyl, alkynyl, cycloalkyl, alkoxy, substituted alkyl, thioalkyl, haloalkyl (including perhaloalkyl), hydroxyalkyl, aminoalkyl, substituted alkenyl, substituted alkynyl, substituted cycloalkyl, aryl, substituted aryl, heteroaryl, substituted heteroaryl, heterocycle, substituted heterocycle, —NR$^e$R$^f$, —NR$^e$C(=O)R$^f$, —NR$^e$C(=O)NR$^e$R$^f$, —NR$^e$C(=O)OR$^f$—NR$^e$SO$_2$R$^f$, —OR$^e$, —C(=O)R$^e$—C(=O)OR$^e$, —C(=O)NR$^e$R$^f$, —OC(=O)NR$^e$R$^f$, —SR$^e$, —SOR$^e$, —S(=O)$_2$R$^e$, —OS(=O)$_2$R$^e$, —S(=O)$_2$OR$^e$, wherein R$^e$ and R$^f$ are the same or different and independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocycle, substituted heterocycle.

The term "halo" or "halogen" as used herein means fluoro, chloro, bromo or iodo.

The term "a" as used herein means one or more.

Reference to "about" a value or parameter herein includes (and describes) embodiments that are directed to that value or parameter per se, and in one embodiment plus or minus 20% of the given value. For example, description referring to "about X" includes description of "X".

"Pharmaceutically acceptable salts" include both acid and base addition salts. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

Compounds of the present invention, unless otherwise indicated, include compounds that differ only in the presence of one or more isotopically enriched atoms. For example, compounds of the present invention, wherein one or more hydrogen atoms are replaced by deuterium or tritium, or one or more carbon atoms are replaced by a $^{13}$C or $^{14}$C carbon atom, or one or more nitrogen atoms are replaced by a $^{15}$N nitrogen atom, or one or more sulfur atoms are replaced by a $^{33}$S, $^{34}$S or $^{36}$S sulfur atom, or one or more oxygen atoms are replaced by a $^{17}$O or $^{18}$O oxygen atom are within the scope of this invention.

One aspect includes a process comprising, contacting a compound of formula IV, or a salt thereof:

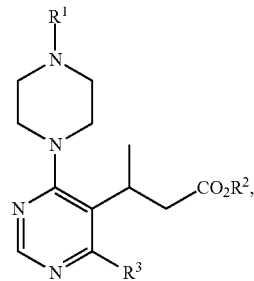

IV wherein
$R^1$ is hydrogen or an amino protecting group;
$R^2$ is hydrogen or optionally substituted $C_1$-$C_{12}$ alkyl; and
$R^3$ is halogen,
with carbon monoxide, carbonylation catalyst and alcohol of formula $R^4$OH to form a compound of formula III, or a salt thereof:

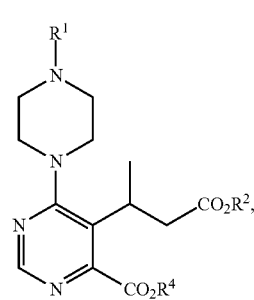

III wherein
$R^4$ is $C_1$-$C_6$ alkyl.

In certain embodiments, the carbonylation catalyst used to form a compound of formula III is a transition metal catalyst, for example, a palladium catalyst (e.g., Pd(OAc)$_2$ plus dppp). In another example, the carbonylation catalyst is a mixture of a ligand metal chloride ([LnM]Cl) (where the ligand is for example (S)- or (R)-α,α-bis[3,5-bis(trifluoromethyl)phenyl]-2-pyrrolidinemethanol trimethylsilyl ether, and the metal is for example Al or Cr), and NaCo(CO)$_4$. In one example, the carbonylation reaction is run in a polar aprotic solvent, such as THF or dimethoxy ethane ("DME" or "glyme"). In one example, the carbonylation reaction is run under increased pressure of CO gas, for example, from about 100 psi to about 1000 psi.

In certain embodiments, $R^1$ is hydrogen.

In certain embodiments, $R^1$ is an amino protecting group. In certain embodiments, $R^1$ is Ac, trifluoroacetyl, phthalimide, Bn, Tr, benzylidenyl, p-toluenesulfonyl, Pmb, Boc, Fmoc or Cbz. In certain embodiments, $R^1$ is Boc group.

In certain embodiments, $R^2$ is hydrogen.

In certain embodiments, $R^2$ is ethyl.

In certain embodiments, $R^2$ is $C_1$-$C_{12}$ alkyl optionally substituted by halogen or phenyl. In certain embodiments, $R^2$ is $C_1$-$C_{12}$ alkyl. In certain embodiments, $R^2$ is methyl, benzyl, ethyl, propyl or butyl. In certain embodiments, $R^2$ is methyl or benzyl. In certain embodiments, $R^2$ is hydrogen, benzyl, ethyl, propyl or butyl.

In certain embodiments, $R^3$ is Cl, Br or I. In certain embodiments, $R^3$ is Cl.

In certain embodiments, $R^4$ is $C_1$-$C_{12}$ alkyl. In certain embodiments, $R^4$ is isopropyl.

In certain embodiments, $R^1$ is amino protecting group, $R^2$ is $C_1$-$C_{12}$ alkyl optionally substituted by phenyl, $R^3$ is halogen and $R^4$ is $C_1$-$C_{12}$ alkyl.

In certain embodiments, $R^1$ is Boc protecting group, $R^2$ is methyl or benzyl, $R^3$ is Cl and $R^4$ is isopropyl.

In certain embodiments, the compound of formula IV comprises a compound of formula IVa

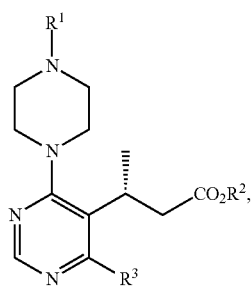

IVa wherein $R^1$, $R^2$ and $R^3$ are as defined in formula IV.

In certain embodiments, in the compound of formula IVa, $R^1$ is Boc protecting group, $R^2$ is methyl or benzyl and $R^3$ is Cl.

In certain embodiments of formula IVa, $R^2$ is not methyl. In certain embodiments of formula IVa, $R^2$ is hydrogen. In certain embodiments of formula IVa, $R^2$ is $C_1$-$C_{12}$ alkyl optionally substituted by halogen or phenyl. In certain embodiments of formula IVa, $R^2$ is $C_1$-$C_{12}$ alkyl. In certain embodiments of formula IVa, $R^2$ is methyl, benzyl, ethyl, propyl or butyl. In certain embodiments of formula IVa, $R^2$ is methyl or benzyl. In certain embodiments of formula IVa, $R^2$ is benzyl, ethyl, propyl or butyl. In certain embodiments of formula IVa, $R^2$ is ethyl.

In certain embodiments, the compound of formula III comprises a compound of formula IIIa:

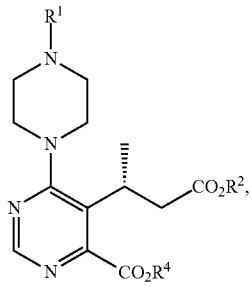

IIIa wherein $R^1$, $R^2$ and $R^4$ are as defined in formula III.

In certain embodiments, in a compound of formula IIIa, $R^1$ is Boc protecting group, $R^2$ is methyl or benzyl and $R^4$ is isopropyl.

In certain embodiments of formula IIIa, $R^2$ is not methyl. In certain embodiments of formula IIIa, $R^2$ is hydrogen. In certain embodiments of formula IIIa, $R^2$ is $C_1$-$C_{12}$ alkyl optionally substituted by halogen or phenyl. In certain embodiments of formula IIIa, $R^2$ is $C_1$-$C_{12}$ alkyl. In certain embodiments of formula IIIa, $R^2$ is methyl, benzyl, ethyl, propyl or butyl. In certain embodiments of formula IIIa, $R^2$ is methyl or benzyl. In certain embodiments of formula IIIa, $R^2$ is benzyl, ethyl, propyl or butyl. In certain embodiments of formula IIIa, $R^2$ is ethyl.

Another aspect includes the compound of formula III or IIIa, or a salt thereof, prepared according to the process of contacting a compound of formula IV or IVa, or a salt thereof with carbon monoxide, carbonylation catalyst and alcohol of formula $R^4$OH.

Another aspect includes a process comprising (i) reacting a compound of formula III, or salt thereof, with base to form an intermediate; and (ii) decarboxylating the intermediate to produce a compound of formula II or salt thereof.

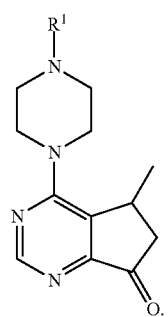

II wherein $R^1$ is as defined in formula IV.

In certain embodiments, the base reacted with formula III comprises a non-nucleophilic base. In certain embodiments, the base comprises hydroxide, alkoxide, lithium alkyl bases or lithium amide bases. In certain embodiments, the base comprises lithium diisopropylamide, t-butyl lithium, sodium t-butoxide, potassium t-butoxide, ammonium t-butoxide, sodium hydroxide, potassium hydroxide or ammonium hydroxide. In certain embodiments, the base comprises potassium t-butoxide. In certain embodiments, the basic conditions further comprise a solvent such as a polar solvent, selected from ethers or other suitable solvents or combinations thereof. In one example, the solvent is THF.

In certain embodiments, the decarboxylating further comprises a catalyst for example, a hydrogenation catalyst, such as palladium catalyst (e.g., Pd on carbon or alumina). In one example, the decarboxylating further comprises a hydrogen or hydride source.

Sources of hydrogen include hydrogen gas, and other sources used in transfer hydrogenation reactions, including water (optionally with formate or acetate salts such as sodium formate), diimide, hydrazine (or hydrazine hydrate), alcohols, such as methanol, ethanol and isopropanol, cycloalkenes, such as cyclohexene, cyclohexadiene, dihydronaphthalene and dihydroanthracene, organic acids (optionally with an amine such as trimethyl or triethylamine), such as formic acid, acetic acid or phosphoric acid, silanes such as $HSiR_3$ (where R is independently an alkyl group, such as $HSiMe_3$ and $HSiEt_3$), NADH, NADPH, $FADH_2$, ammonium salts, such as ammonium formate and ammonium chloride, and Hanztch esters such as those of the formula:

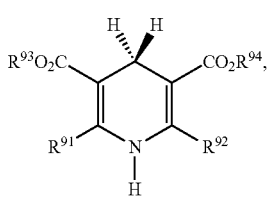

wherein $R^{91}$, $R^{92}$, $R^{93}$ and $R^{94}$ are independently alkyl (In certain examples: $R^{91}$ and $R^{92}$ are methyl and $R^{93}$ and $R^{94}$ are ethyl; $R^{91}$ and $R^{92}$ are methyl and $R^{93}$ and $R^{94}$ are butyl; $R^{91}$ is methyl, $R^{92}$ is isopropyl and $R^{93}$ and $R^{94}$ are methyl; $R^{91}$ and $R^{92}$ are methyl, $R^{93}$ is methyl and $R^{94}$ is t-butyl; $R^{91}$, $R^{92}$, $R^{93}$ and $R^{94}$ are methyl; $R^{91}$ and $R^{92}$ are methyl and $R^{93}$ and $R^{94}$ are isobutyl; $R^{91}$ and $R^{92}$ are methyl and $R^{93}$ and $R^{94}$ are allyl).

In certain embodiments, the compound of formula II comprises a compound of formula IIa:

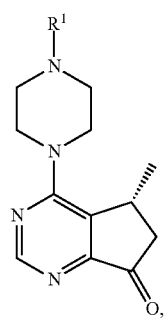

IIa wherein $R^1$ is as defined in formula II.

In certain embodiments, the intermediate includes a compound of formula:

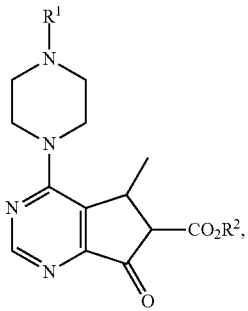

wherein $R^1$ and $R^2$ are defined as they are for compounds of formula IV.

In certain embodiments, the intermediate includes a compound of formula:

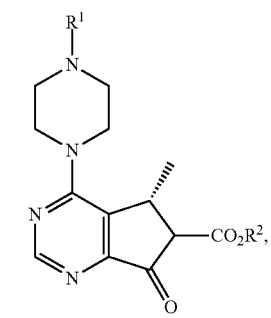

wherein $R^1$ and $R^2$ are defined as they are for compounds of formula IV.

Another aspect includes the compound of formula II or IIa, or a salt thereof, prepared according to the process of (i) reacting a compound of formula III or IIIa, or salt thereof, with base to form an intermediate; and (ii) decarboxylating the intermediate.

Another aspect includes a process comprising reducing a compound of formula II, or a salt thereof, to form a compound of formula I, or a salt thereof:

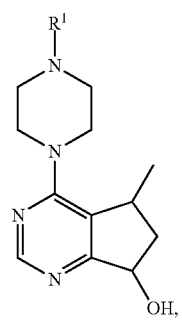

I wherein $R^1$ is as defined for formula IV.

In certain embodiments, the reducing reaction comprises reducing a compound of formula IIa or salt thereof to form a compound of formula Ia, or a salt thereof:

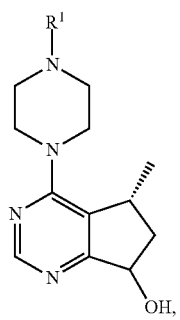

Ia wherein R¹ is as defined as for compounds of formula IV.

The process for preparing a compound of formula I, or a salt thereof, by reducing a compound of the formula II, or a salt thereof, may be carried out under reaction conditions that, for example, include a suitable base (e.g., an inert amine base, such as a trialkylamine base, such as triethylamine) and in a suitable solvent (e.g., a polar aprotic solvent such as glyme, diglyme, THF or dichloromethane).

In some embodiments, the reducing of formula II or IIa comprises a reducing reagent capable of reducing a ketone to an alcohol, such as a metal hydride (e.g., a boron, aluminum or lithium/aluminum hydride) reducing agent. In one aspect, the reducing agent promotes asymmetric reduction. The reducing agent may contain one or more compounds or components, such as when a reagent that is capable of hydrogen or hydride transfer is used in conjunction with an agent that promotes or directs stereoselectivity of the hydrogen or hydride transfer reaction, e.g., a stereoselective catalyst or enzyme. Thus, in one aspect, the reducing agent is a stereoselective reducing reagent comprising an agent that is capable of hydrogen or hydride transfer and an agent that promotes or directs stereoselectivity of the hydrogen or hydride transfer reaction. In one aspect, the agent that promotes or directs stereoselectivity of the hydrogen or hydride transfer reaction is a catalyst, such as a metal catalyst (e.g., a transition metal catalyst). In one aspect, the agent that promotes or directs stereoselectivity of the hydrogen or hydride transfer reaction is an enzyme.

In certain embodiments, the reaction of a compound of formula II or IIa, or a salt thereof, with a reducing agent to provide a compound of formula I or Ia, or a salt thereof, is carried out by a catalytic reduction reaction wherein the catalyst comprises a metal catalyst such as a ruthenium catalyst, a rhodium catalyst or a palladium catalyst to produce one or more chiral centers. Examples of metal catalysts include, but are not limited to, $RuL_3X$ (wherein X is a halogen, e.g., Cl) or $RhL_3Cl$, wherein L is a phosphine ligand, such as $PR_3$, wherein R is independently alkyl, alkenyl, alkynyl, cycloalkyl, aryl or heterocyclyl, and wherein R is independently optionally substituted, such as [RhCl(PPh$_3$)$_3$].

Examples of ligands for the metal catalyst include, but are not limited to DIOP, DIPAMP, BINAP, TolBINAP, XylBINAP, BPPFOH, BPPM, BICHEP, BPPFOH, BICHHEP, BIPHEP, BIPHEMP, MeO-BIPHEP, MOD-DIOP, CyDIOP, BCPM, MCCPM, NORPHOS, PYRPHOS (DEGUPHOS), BDPP (SKEWPHOS), Me-DuPhos, Et-DuPhos, iPr-DuPhos, Me-BPE, Et-BPE, iPr-BPE, o-Ph-HexaMeO-BIPHEP, RoPHOS, KetalPhos, BASPHOS, Me-PennPhos, BINAPHANE, BICP, DIOP, BDPMI, T-Phos, SK-Phos, EtTRAP, PrTRAP, PrTRAP, BuTRAP, PhTRAP, Josiphos, PPF-tBu$_2$, Xyliphos, FerroPHOS, FERRIPHOS, TaniaPhos, f-KetalPHos, Et-FerroTANE, t-Bu-BISP, Ad-BisP, Cy-BisP, t-Bu-MiniPhos, Cy-MiniPhos, iPr-MiniPhos, TangPhos, BIPNOR, Binapine, unsymmetrical BisP, [2,2]PHANEPHOS, Ph-o-NAPHOS, spirOP, BINAPO, Ph-o-BINAPO, DIMOP, and others described in Chi, Y, et. al, Modern Rhodium-Catalyzed Organic Reactions, Ed. Evans, P. A., Wiley, 2005, Chapter 1.

Examples of metal catalysts include, but are not limited to [(S)-BINAPRuCl(benzene)]Cl, [(R,R)TsDACH Ru(p-cymene)Cl] and [(R,R)Teth-TsDPEN RuCl] or (R,R) Me$_2$NSO$_2$DPEN with [RhCp*Cl$_2$]$_2$. In another example, the catalyst is a heterogeneous hydrogenation catalyst for example palladium on carbon or palladium on aluminum oxide. In one example, the catalyst is 5% Pd/C Type A405038 or 5% Pd/Al$_2$O$_3$ Type A302011 to produce the cis isomer. Other suitable catalyst may be identified by screening, e.g., based on desired stereoselectivity, reaction rate and turnover. The reducing agent may comprise any suitable hydrogen source or hydride source, such as formic acid or a boron reducing agent or hydrogen gas.

In some examples, a hydrogen source is used in combination with a metal catalyst comprising magnesium, sodium, ruthenium(II), rhodium(III), iridium(III), nickel, platinum, palladium or a combination thereof.

In some embodiments, the reaction of a compound of formula II or IIa, or a salt thereof, with a reducing agent to provide a compound of formula I or Ia, or a salt thereof, is carried out by a catalytic reduction reaction wherein the catalyst is a metal catalyst such as a ruthenium catalyst or a rhodium catalyst to produce the trans isomer, for example, [(R,R)TsDACH Ru(p-cymene)Cl] and [(R,R)Teth-TsDPEN RuCl] or (R,R)Me$_2$NSO$_2$DPEN with [RhCp*Cl$_2$]$_2$. In another example, the catalyst is a heterogeneous hydrogenation catalyst for example palladium on carbon or palladium on aluminum oxide. In one example of reducing of formula II compounds, the catalyst is 5% Pd/C Type A405038 or 5% Pd/Al$_2$O$_3$ Type A302011 to produce the cis isomer. Other suitable catalyst may be identified by screening, e.g., based on desired stereoselectivity, reaction rate and turnover. The reducing agent may comprise any suitable hydrogen source or hydride source, such as formic acid or a boron reducing agent or hydrogen gas.

Another aspect includes the compound of formula I or Ia, or a salt thereof, prepared according to the process of reducing a compound of formula II or IIa, or a salt thereof. Another aspect includes a process of preparing a compound of formula X or a salt thereof

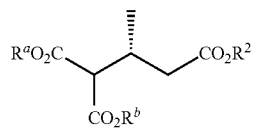

X wherein $R^a$ and $R^b$ are independently $C_{1-12}$ alkyl; and $R^2$ is hydrogen or optionally substituted $C_1$-$C_{12}$ alkyl, the process comprising contacting a compound of formula XI with a lipase to form the compound of formula X:

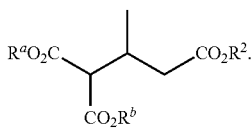

In certain embodiments of formulas X and XI, $R^a$, $R^b$ and $R^2$ are methyl. In certain embodiments of formulas X and XI, $R^a$ and $R^b$ are methyl and $R^2$ is hydrogen, methyl, ethyl, propyl or butyl. In certain embodiments of formulas X and XI, $R^a$ and $R^b$ are methyl and $R^2$ is hydrogen. In certain embodiments of formulas X and XI, $R^a$ and $R^b$ are methyl and $R^2$ is propyl. In certain embodiments of formulas X and XI, $R^a$ and $R^b$ are methyl and $R^2$ is methyl or ethyl. Examples of the lipase include an enzyme originated from a microorganism of *Candida* such as *Candida cylindracea* and *Candida rugosa*, a microorganism of *Chromobacterium chocolatum*, pig liver and a thermophilic microorganism.

Additional examples of the lipase include an enzyme originated from *Chromobacterium* strain SC-YM-1 (FERM BP-6703) and commercially available enzymes CHIRAZYME E-3 (originated from thermophilic microorganism), lipase CHIRAZYME L-3 (originated from *Candida rugosa*), cholesterol esterase (originated from *Candida cylindracea*) (Roche Diagnostics), lipase ChiroCLEC-CR (Altus Biologics), lipase Lipase-MY (*Candida cylindracea*) (Meito Sangyo Co., Ltd.), and lipase Lipase OF (Meito Sangyo Co., Ltd.) and PLEA (Amano Enzyme Inc.).

Additional examples of lipase include include an enzyme originated from a microorganism of *Bacillus* such as *Bacillus licheniformis* and *Bacillus subtilis*, a microorganism of *Arthrobacter globiformis*, a microorganism of *Candida antactica*, bovine pancreas and a thermophilic microorganism.

Additional examples of lipase include an enzyme originated from *Arthrobacter* strain SC-6-98-28 (FERM BP-3658), and commercially available enzymes such as esterase CHIRAZYME E-4 (originated from thermophilic microorganism), protease CHIRAZYME P-1 (originated from *Bacillus licheniformis*) (Roche Diagnostics), protease Purafect 4000E (GENENCOR), protease α-Chymotrypsin (SIGMA), and lipase SP-525 (Novozymes Japan). Another aspect includes the compound of formula X or salt thereof prepared according to the process of contacting a compound of formula XI with a lipase.

Another aspect includes a process of reacting a compound of formula X or a salt thereof with formamidine to form a compound of formula XII or a salt thereof,

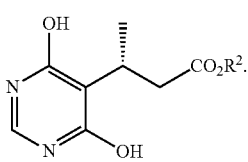

Another aspect includes the compound of formula XII, or salt thereof, prepared according to the process of reacting a compound of formula X or salt thereof with formamidine. In certain embodiments of formulas XII and XIII, $R^2$ is hydrogen, methyl, ethyl, propyl or butyl. In certain embodiments of formulas XII and XIII, $R^2$ is hydrogen, ethyl, propyl or butyl. In certain embodiments of formulas XII and XIII, $R^2$ is methyl. In certain embodiments of formulas XII and XIII, $R^2$ is hydrogen. In certain embodiments of formulas XII and XIII, $R^2$ is propyl. In certain embodiments of formulas XII and XIII, $R^2$ is methyl or ethyl.

Another aspect includes a process comprising chlorinating a compound of formula XII or a salt thereof to form a compound of formula XIII, or a salt thereof.

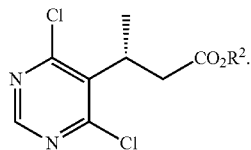

Anothere aspect includes a compound of formula XIII or salt thereof prepared according to the process of chlorinating a compound of formula XII or salt thereof.

Another aspect includes a processes comprising contacting a compound of formula XIII or a salt thereof, with a compound

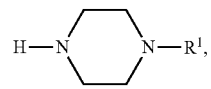

to form a compound of formula IV or salt thereof.

Clorinating agents include, for example, $PCl_3$, $PCl_5$, $O{=}PCl_3$, $P(OH)Cl_3$, $Cl_2$ (in one example with a phosphine, such as $PR_3$ wherein R is an alkyl, cycloalkyl, aryl or heterocyclyl group), HCl, $O{=}SCl_2$, other chloride salts such as NaCl, KCl and $CuCl_2$ (in one example with fluorinating agents such as 1-chloromethyl-4-fluoro-1,4-diazoniabicyclo[2.2.2]octane bis(tetrafluoroborate) or Selectfluor®).

Another aspect includes a process for producing a compound of formula I or Ia, or a salt thereof, comprising (1) contacting a compound of the formula IV or IVa, or a salt thereof, with carbon monoxide, carbonylation catalyst and alcohol to form a compound of the formula III or IIIa, or a salt thereof; (2) contacting the compound of the formula III or IIIa, or salt thereof, with a base to form an intermediate compound; (3) decarboxylating the intermediate compound to form a compound of the formula II or IIa, or a salt thereof; and (4) reducing the compound of formula II or IIa, or a salt thereof, to form a compound of formula I or Ia.

Another aspect includes the compound of formula IV or IVa, or a salt thereof, produced according to the process of contacting a compound of formula XIII or salt thereof, with a compound

The compounds detailed herein may contain one or more chiral centers. Accordingly, if desired, such compounds can be prepared or isolated as pure stereoisomers (such as individual enantiomers or diastereomers, or as stereoisomer-enriched mixtures). All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic or stereoisomer-enriched mixtures of such compounds can be separated using, for example, chiral column chromatography, chiral resolving agents, and the like.

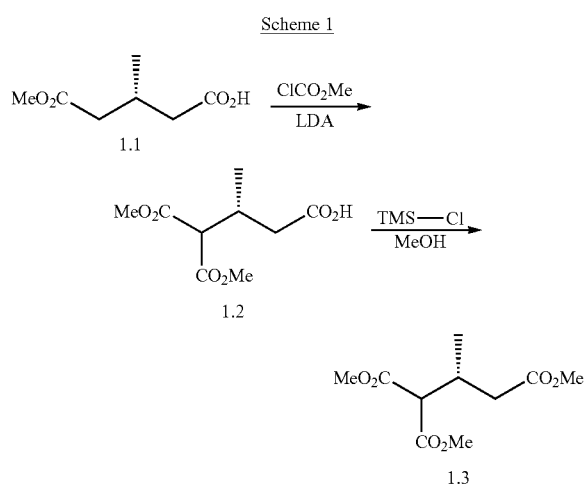

Scheme 1 illustrates an exemplary method for making a compound of the formula 1.3. Starting from (R)-5-methoxy-3-methyl-5-oxopentanoic acid, reaction with methyl chloroformate gives (R)-5-methoxy-4-(methoxycarbonyl)-3-methyl-5-oxopentanoic acid, which can be esterified with, for example, trimethylsilyl chloride and methanol to give compound 1.3, (R)-trimethyl 2-methylpropane-1,1,3-tricarboxylate.

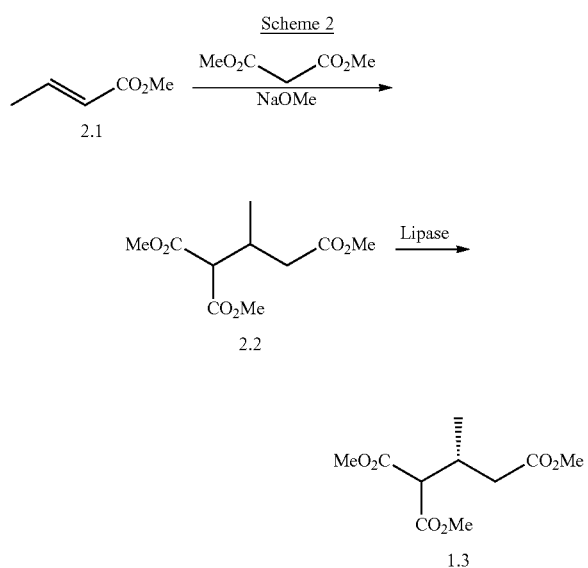

Scheme 2 illustrates an alternative exemplary method for making a compound of the formula 1.3. Starting from (E)-methyl but-2-enoate, reaction with dimethyl malonate and sodium methoxide gives trimethyl 2-methylpropane-1,1,3-tricarboxylate, which can be resolved, by for example, a lipase, to give compound 1.3.

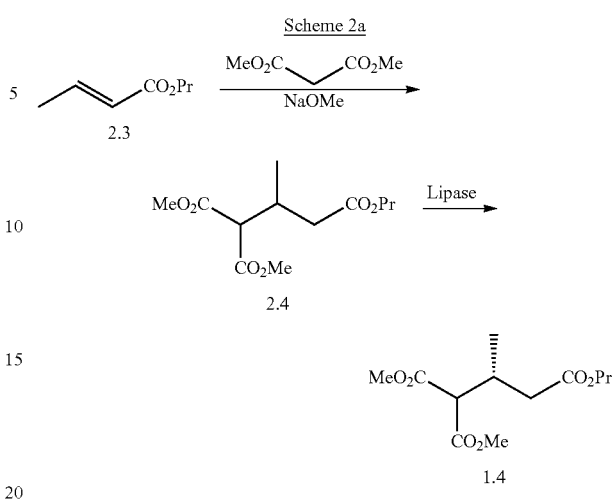

Scheme 2a illustrates an alternative exemplary method for making a compound of the formula 1.4. Starting from (E)-methyl but-2-enoate, reaction with dimethyl malonate and sodium methoxide gives compounds of formula 2.4, which can be resolved, by for example, a lipase, to give compounds of formula 1.4.

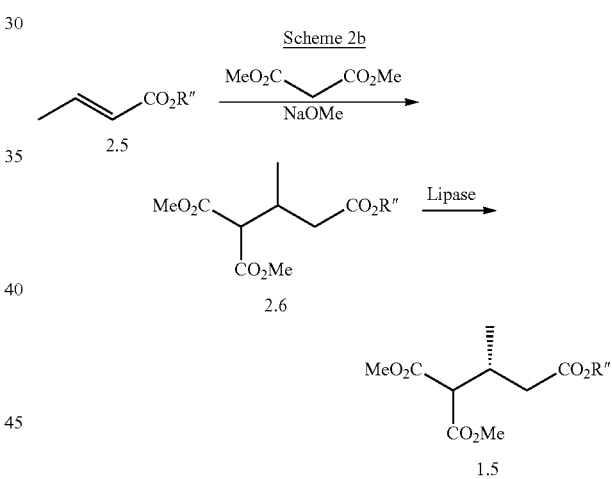

wherein R' is methyl or ethyl

Scheme 2b illustrates an alternative exemplary method for making compounds of formula 1.5. Starting from (E)-methyl but-2-enoate, reaction with dimethyl malonate and sodium methoxide gives compounds of formula 2.6, which can be resolved, by for example, a lipase, to give compounds of formula 1.5.

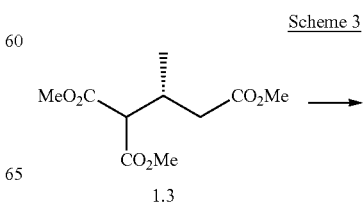

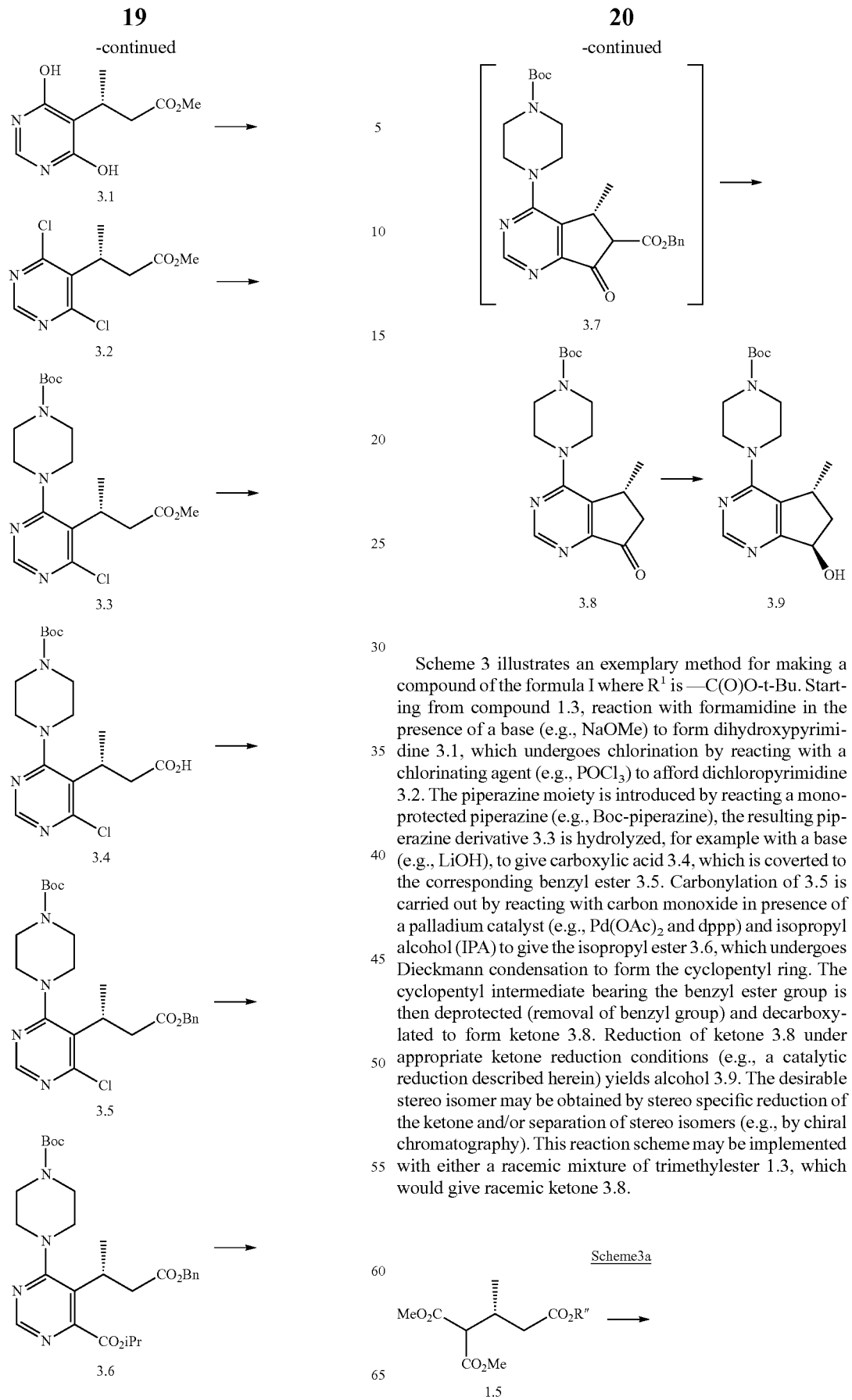

Scheme 3 illustrates an exemplary method for making a compound of the formula I where R¹ is —C(O)O-t-Bu. Starting from compound 1.3, reaction with formamidine in the presence of a base (e.g., NaOMe) to form dihydroxypyrimidine 3.1, which undergoes chlorination by reacting with a chlorinating agent (e.g., POCl₃) to afford dichloropyrimidine 3.2. The piperazine moiety is introduced by reacting a mono-protected piperazine (e.g., Boc-piperazine), the resulting piperazine derivative 3.3 is hydrolyzed, for example with a base (e.g., LiOH), to give carboxylic acid 3.4, which is coverted to the corresponding benzyl ester 3.5. Carbonylation of 3.5 is carried out by reacting with carbon monoxide in presence of a palladium catalyst (e.g., Pd(OAc)₂ and dppp) and isopropyl alcohol (IPA) to give the isopropyl ester 3.6, which undergoes Dieckmann condensation to form the cyclopentyl ring. The cyclopentyl intermediate bearing the benzyl ester group is then deprotected (removal of benzyl group) and decarboxylated to form ketone 3.8. Reduction of ketone 3.8 under appropriate ketone reduction conditions (e.g., a catalytic reduction described herein) yields alcohol 3.9. The desirable stereo isomer may be obtained by stereo specific reduction of the ketone and/or separation of stereo isomers (e.g., by chiral chromatography). This reaction scheme may be implemented with either a racemic mixture of trimethylester 1.3, which would give racemic ketone 3.8.

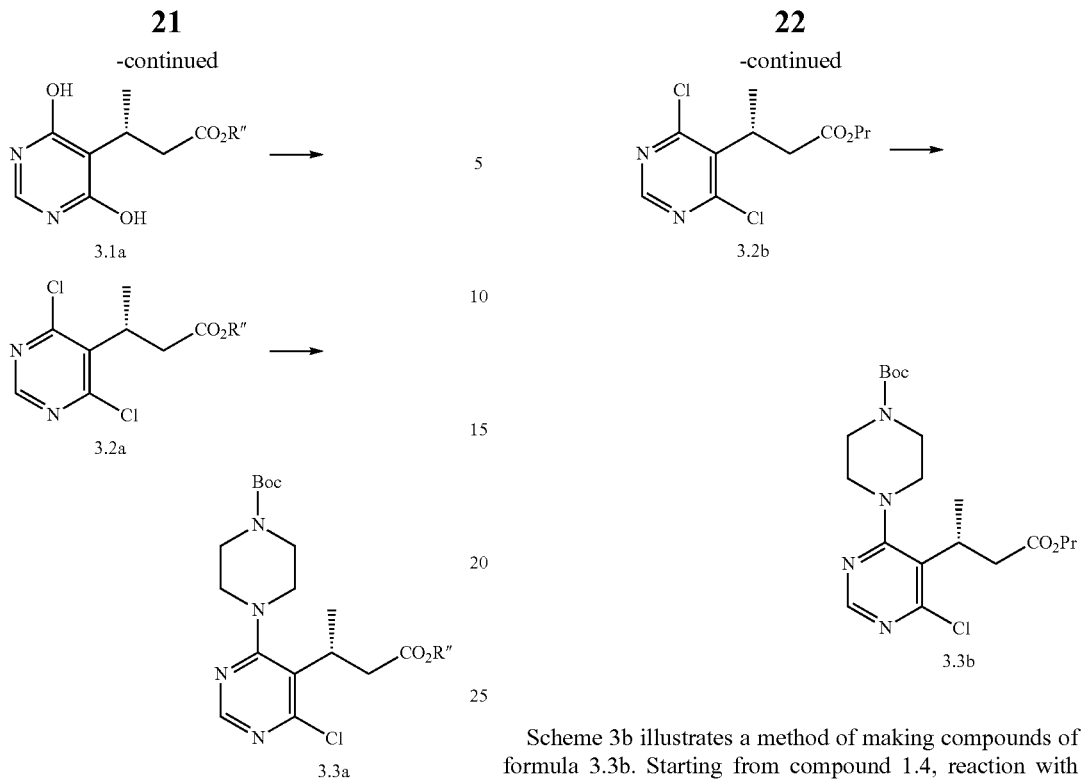

Scheme 3a illustrates a method of making compounds of formula 3.3a. Starting from compound 1.5, reaction with formamidine in the presence of a base (e.g., NaOMe) to form dihydroxypyrimidine 3.1a, which undergoes chlorination by reacting with a chlorinating agent (e.g., $POCl_3$) to afford dichloropyrimidine 3.2a. The piperazine moiety is introduced by reacting a mono-protected piperazine (e.g., Boc-piperazine) to give the resulting piperazine derivative 3.3a. Compounds of formula 3.3a can be used to make compounds of formula 3.9, according to Scheme 3.

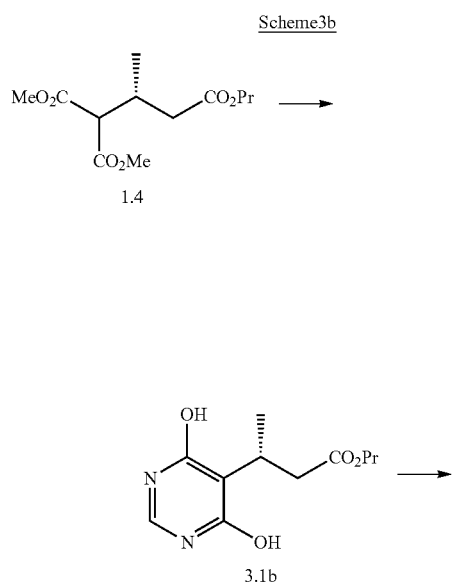

Scheme 3b illustrates a method of making compounds of formula 3.3b. Starting from compound 1.4, reaction with formamidine in the presence of a base (e.g., NaOMe) to form dihydroxypyrimidine 3.1b, which undergoes chlorination by reacting with a chlorinating agent (e.g., $POCl_3$) to afford dichloropyrimidine 3.2b. The piperazine moiety is introduced by reacting a mono-protected piperazine (e.g., Boc-piperazine) to give the resulting piperazine derivative 3.3b. Compounds of formula 3.3a can be used to make compounds of formula 3.9, according to Scheme 3.

Another aspect provides the use of compounds of formula I as intermediates for preparing pharmaceutically active compounds, such as the AKT inhibitors described in U.S. Pat. No. 8,063,050, issued Nov. 22, 2011 to Mitchell. For example, as shown below in Scheme 4, compounds of formula I can be used to prepare (S)-2-(4-chlorophenyl)-1-(4-((5R,7R-7-hydroxy-5-methyl-6,7-dihydro-5H-cyclopenta[d]pyrimidin-4-yl)piperazin-1-yl)-3-(isopropylamino)propan-1-one, as described in U.S. Pat. No. 8,063,050, issued Nov. 22, 2011, as described, for example, in Example 14, which is incorporated herein by reference.

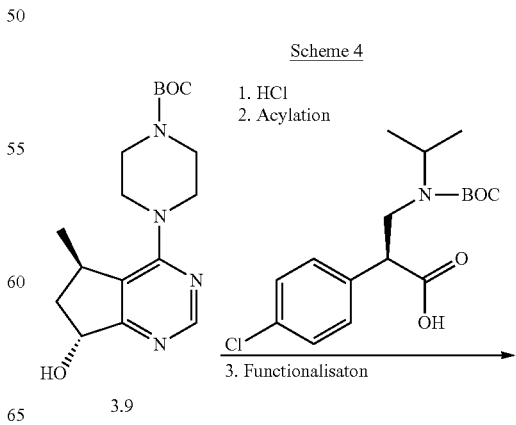

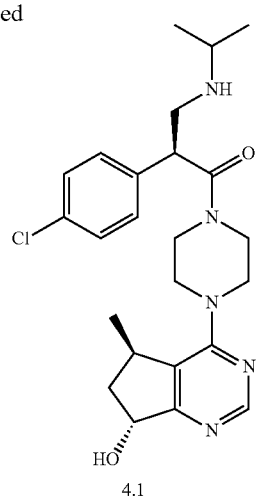

4.1

Scheme 4 illustrates a method for making a compound of formula 4.1. Deprotection of compound 3.9 using acid, followed by acylation/coupling with the amino acid, or a salt thereof, and finally deprotection of the remaining Boc group with acid gives compound 4.1.

EXAMPLES

The invention can be further understood by reference to the following examples, which are provided by way of illustration and are not meant to be limiting.

Abbreviations used herein are as follows:
Aq.: aqueous
DIPA: diisopropylamine
DIPEA: diisopropylethylamine
MTBE: methyl t-butyl ether
TMSCl: chlorotrimethylsilane
MsDPEN: N-methanesulfonyl-1,2-diphenylethylenediamine
TsDACH: N-(p-toluenesulfonyl)-1,2-diaminocyclohexane
Dppp: 1,3-Bis(diphenylphosphino)propan
NMM: 4-methylmorpholine
T3P: 1-propanephosphonic anhydride
HBTU: 2-(1H-benzotriazole-1-yl)-1,1,3,3-tetramethyluronium hexafluorophosphate
PhME: toluene
CPME: Cyclopentyl methyl ether
DBU: 1,8-Diazobicyclo[5,40]undec-7-ene
CDI: 1,1'-carbonyldiimidazole
THF: tetrahydrofuran
min: minutes
h: hours
TLC: thin layer chromatography Example 1

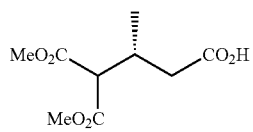

(R)-5-methoxy-4-(methoxycarbonyl)-3-methyl-5-oxopentanoic acid

To a 250 mL round-bottomed flask equipped with a stirbar and purged with nitrogen, was added 30 mL anhydrous THF followed by DIPA (2.21 g, 3.5 eq, 21.85 mmol). The mixture was cooled to −78° C. with stirring, n-BuLi (2.5 M, 3.3 eq, Aldrich) was then added dropwise, and the reaction was stirred for 10 min. To the flask was slowly added (R)-5-methoxy-3-methyl-5-oxopentanoic acid (1 g, 6.25 mmol, in 10.0 mL THF, Sumitomo) over about 2 min. After 30 min stirring at −78° C., a solution of methyl chloroformate (2.1 eq, 13.13 mmol) in THF (10 mL) was slowly added to the mixture. After the addition was complete, the reaction mixture was allowed warm to room temperature overnight. The reaction mixture was adjusted to about pH 5 to 6 (using pH paper), with cooling to maintain about ambient temperature using 2N aq. HCl. The reaction mixture was concentrated under reduced pressure, diluted with 75 mL EtOAc and 25 mL aq. 1N HCl. The layers were separated and the aqueous phase was extracted (2×15 mL EtOAc). The combined organics were washed with saturated aqueous NaCl (1×15 mL), dried over MgSO$_4$, and concentrated under reduced pressure to give the product (1.36 g), which was used in the subsequent step without purification.

Example 2

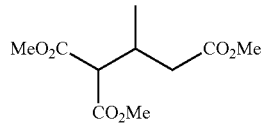

trimethyl 2-methylpropane-1,1,3-tricarboxylate

To a mixture of 28% NaOMe/methanol (0.25 eq) and dimethyl malonate (1.0 eq) in methanol (1.6 vol) was added methyl crotonate at 70° C. The reaction mixture was stirred at the same temperature for 2 hr. After neutralization with acetic acid (0.25 eq)/water (50/50) at 25° C., the mixture was concentrated under reduced pressure. To the mixture was added 5% aq NaCl (3.82 vol) and extracted with MTBE (2 vol X 2), washed two times with 10% NaCl (2 vol) and concentrated to give the product as an oil (89.1% yield, 95% pure as measured by GC-MS).

Example 3

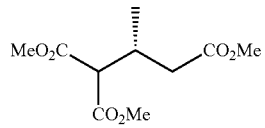

(R)-trimethyl 2-methylpropane-1,1,3-tricarboxylate

Example 3.1

Method 1

A 100 mL round-bottom flask equipped with a stirbar, (R)-5-methoxy-4-(methoxycarbonyl)-3-methyl-5-oxopentanoic acid (1.36 g, 6.24 mmol), and was purged with nitrogen. The reaction mixture was charged with MeOH (30 mL) and TMSCl (2.0 eq, 1.58 mL) was added dropwise (neat) via syringe. The mixture was allowed to stir for 18 hr. The reaction was concentrated under reduced pressure to afford an oil. The residue was then dissolved in 10 mL anhydrous toluene and concentrated under reduced pressure in order to azeotropically remove water generated during the reaction. The crude product was dissolved in 10 mL anhydrous MeOH and concentrated under reduced pressure to remove toluene. The product was used (quant. yield assumed) in subsequent steps without further purification.

Example 3.2

Method 2

To the phosphate buffer (10 vol) with pH between about 7.0 to 7.1, the trimethyl 2-methylpropane-1,1,3-tricarboxylate (1000 g) and the lipase enzyme (30 g, Lipase AY Amano 30G, Anamo Enzyme, Inc.) was added. The mixture was stirred at a temperature of about 40 to 45° C. with adjustment to pH between about 7.0 to 7.1 until the reaction was deemed completed by HPLC (about 6 days). The reaction mixture was adjusted to pH about 3 to 4 with 2M HCl, Celite® and MTBE (5 vol) were added, and the mixture was filtered and extracted twice with MTBE (3 vol). The combined organics were washed with 5% NaHCO$_3$ and concentrated under reduced pressure to give final product as oil (273 g, 27% yield, 98% ee).

Example 4

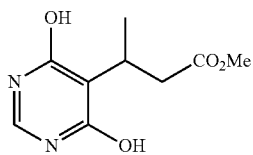

Methyl 3-(4,6-dihydroxypyrimidin-5-yl)butanoate

A 12-L, 4-necked reactor, equipped with a mechanical stirrer, was charged with 2.80 L of methanol and sparged with nitrogen. The solvent was treated with NaOMe (1969 mL, 8612 mmol) and transfer washed with 250 mL of methanol. The mixture was left to stir for 1.5 hours before the solution was treated with formamidine acetate (246.6 g, 2368 mmol) in one sum (granular-homogenized). The mixture was allowed to stir for 20 minutes (the solids dissolved within about 10 minutes post addition) to afford a homogeneous solution. Trimethyl 2-methylpropane-1,1,3-tricarboxylate (500 g, 2153 mmol) was added via dropping funnel as a solution in 500 mL of methanol over a five minute period, followed by 200 mL more of methanol to complete transfer. The reaction (clear, bright yellow) was allowed to stir at ambient temperature overnight to completion as measured by NMR analysis (alliquot of 250 uL was removed via pipet and treated with five drops of aq. 3N HCl, reduced under vacuum to dryness, dissolved in d$_6$-DMSO and then filtered) after 16 hours. The reaction was placed in an ice-bath and cooled to about 3.1° C. over a one hour period. A three-pound bottle of HCl (g) was used to quench the reaction (bubbling gas into solution via teflon tubing) over a one hour ten minute period reaching an endpoint of about pH=2.5 (via paper). The temperature was maintained below about 9.6° C. throughout the addition, and the yellow solution changed to an off-white suspension. The suspension was concentrated using vacuum distillation (35-37° C. @ 200 Torr) of the methanol (removed 3.34 L) in vacuo to afford a white/tan paste. The mixture was suspended in 3.75 L of toluene (7.5× volume) and stirred for 30 minutes. The suspension was filtered off (table top filter/polypropylene cloth, pad washed with 2×500 mL portions of toluene). The pad of product was allowed to air-dry under suction overnight on the filter then broken up with a spatula to give 396.8 grams, 86.9% yield.

Example 5

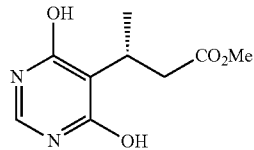

(R)-methyl 3-(4,6-dihydroxypyrimidin-5-yl)butanoate

To the solution of formamidine acetate (1.05 eq) in methanol (5 vol) was added 29.2% NaOMe/methanol (3 eq) at 0° C. for 0.25 h and the mixture was stirred for 0.5 h. To this was added the mixture of (R)-trimethyl 2-methylpropane-1,1,3-tricarboxylate (1.1 kg, 20 L) and methanol (50% w/w) for 0.5 h. After warming to 20° C., the reaction mixture was stirred for 14 h. The reaction mixture was neutralized with 5% aq HCl at 0° C. When pH was about 7, the mixture was concentrated. To the mixture was added methanol (0.7 vol), the mixture was washed with MTBE (5 vol), acidified with HCl to pH about 2 at 2° C., and stirred for 1 h at 60° C. After cooling to 0° C., the mixture was filtered and the cake was washed with water (1 vol) and dried in vacuum at 50° C. to get the product as solid (0.8 kg, 66% yield, 96% purity).

Example 6

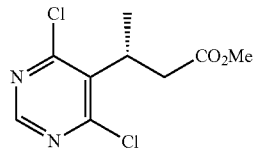

(R)-methyl 3-(4,6-dichloropyrimidin-5-yl)butanoate

A 22 L round bottom flask (equipped with overhead mechanical stirring, condenser, and thermocouple) was charged with (R)-methyl 3-(4,6-dihydroxypyrimidin-5-yl) butanoate (1.00 kg, 4.70 mol) (available from Sumitomo, toluene (4.00 L), and 2,6-lutidine (0.550 L, 4.70 mol) at room temperature. The mixture was stirred and warmed to 50° C. Phosphorous oxychloride (0.960 L, 10.6 mmol) was added slowly via addition funnel (at a rate of about 30.0 mL/min) resulting in a brown mixture. The internal temperature (IT) rose to about 85° C. upon addition of the first 500 mL of POCl₃, but no further exotherm was observed. The IT was allowed to decrease to about 70° C., and this temperature was maintained for 20-24 h, with stirring. Analysis by LC-MS showed clean product formation after 24 h. The solution was allowed to cool to room temperature, and then further coiled to about 0° C. To the mixture was slowly and carefully added 20% aqueous sodium hydroxide (about 40.0 mmol, 1.60 kg in 8.00 L H₂O) via addition funnel while maintaining the internal temperature below 30° C., to obtain a final pH value between about 5 and 6. Ethyl acetate (2.50 L) was added, stirred for 0.5 h, and then the layers were separated. The aqueous phase was extracted with ethyl acetate (3×1.00 L). The organics were combined and washed with 1 N hydrochloric acid (2×2.50 L), and brine (2.50 L).

The organic layers were combined and dried over sodium sulfate and filtered through a glass fiber filter. Quantitative ¹H NMR, using isopropanol as internal standard, indicated about quantitative yield. The solution was concentrated to about 3.00 mL/g, and diluted with acetonitrile to about 7.00 mL/g. The sequence was repeated two times to remove residue ethyl acetate and toluene (confirmed by ¹H NMR analysis). The remaining crude solution was used directly for next step without further purification or isolation.

Example 7

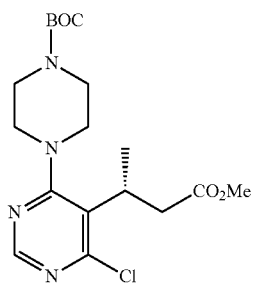 [SMILES: COC(=O)C[C@@H](C)c1c(Cl)ncnc1N1CCN(C(=O)OC(C)(C)C)CC1]

(R)-tert-butyl 4-(6-chloro-5-(4-methoxy-4-oxobutan-2-yl)pyrimidin-4-yl)piperazine-1-carboxylate A 5 L, 3-neck round bottom flask was equipped with a mechanical stirrer, drying tube, nitrogen inlet, thermocouple, and placed in a heating mantle. The flask was charged with tert-butyl piperazine-1-carboxylate (185 g) and Methanol (0.8 L) was added. The reaction mixture was stirred at room temperature until all of the solids are dissolved (about 15 minutes). Methyl 3-(4,6-dichloropyrimidin-5-yl)butanoate (225 g) in methanol (0.6 L) was added. Diisopropylethylamine (173 mL) was added in one portion. The reaction mixture was heated to 50° C. and stirred for 4 h at 50° C. and monitored by TLC. The reaction mixture was cooled to room temperature and concentrated at 35-40° C. under vacuum to a light brown residue. The residue was dissolved in ethyl acetate (2 L) and aqueous saturated ammonium chloride solution (0.5 L was added. The layers were separated, and the organic layer was washed with aqueous saturated ammonium chloride solution (2×0.5 L) and brine (0.5 L), dried using magnesium sulfate, filtered through a glass fiber filer, and the filtrate concentrated at 30-35° C. under vacuum to yield the product as brown viscous oil. Yield=345 g (96%), structure confirmed by ¹H-NMR (CDCl₃).

Example 8

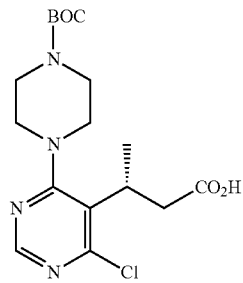 [SMILES: C[C@H](CC(=O)O)c1c(Cl)ncnc1N1CCN(C(=O)OC(C)(C)C)CC1]

(R)-3-(4-(4-(tert-butoxycarbonyl)piperazin-1-yl)-6-chloropyrimidin-5-yl)butanoic acid A 5 L, 3-nech round bottom flask was equipped with a mechanical stirrer, drying tube, nitrogen inlet, thermocouple, and placed in a cooling bath. The flask was charged with a solution of (R)-tert-butyl 4-(6-chloro-5-(4-methoxy-4-oxobutan-2-yl)pyrimidin-4-yl)piperazine-1-carboxylate, Example 7, (345 g) in THF (1.5 L), and stirring was initiated. A solution of LiOH.H₂O (109 g) in water (0.75 L) was added in one portion. The reaction mixture was stirred for 15 hours at room temperature and monitored by TLC. The reaction mixture was cooled to 0° C. and 6N HCl (460 mL) was added slowly dropwise over 20 min. Ethyl acetate (31 L) was added and the reaction mixture was stirred vigorously for 0.5 hour at room temperature. The layers were allowed to separate. The organic layer was collected, and the aqueous layer was extracted with ethyl acetate (3×1 L). The combined organic layers were washed with aqueous saturated ammonium chloride solution (2×1.5 L) and brine (1 L), dried using magnesium sulfate, filtered through a glass fiber filter and the filtrate concentrated at 35-40° C. under vacuum to yield the product as a light pink solid. MTBE (0.5 L) was added, and the mixture was stirred vigorously for 3-4 hours at room temperature. The solids were collected by filtration using a polypropylene filter pad and washed with MTBE (2×150 mL). The filtrate was concentrated at 30-35° C. under vacuum to yield a yellow residue. MTBE (80 mL) was added with stirring, and solids precipitated. The solids were collected by filtration using a polypropylene filter pad and washed with MTBE (2×25 mL). The filtrate was concentrated at 30-35° C. under vacuum to yield a yellow residue. MTBE (40 mL) was added with stirring, and solids precipitated. The solids were collected by filtration using a polypropylene filter pad and washed with MTBE (2×25 mL). The solids were combined

Example 9

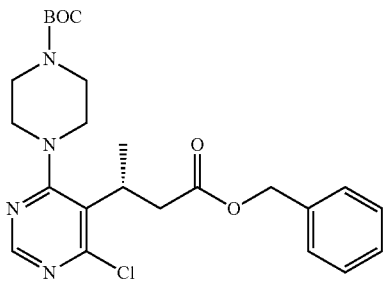 [SMILES: C[C@H](CC(=O)OCc1ccccc1)c1c(Cl)ncnc1N1CCN(C(=O)OC(C)(C)C)CC1]

(R)-tert-butyl 4-(5-(4-(benzyloxy)-4-oxobutan-2-yl)-6-chloropyrimidin-4-yl)piperazine-1-carboxylate As 22 L, 3-neck round bottom flask was equipped with a mechanical stirrer, drying tube, nitrogen inlet, thermocouple and cooling bath. The flask was charged with (R)-3-(4-(4-(tert-butoxycarbonyl)piperazin-1-yl)-6-chloropyrimidin-5-yl)butanoic acid, (2750 g) and dimethylformamide (13.0 L) and stirred. Benzylbromide (891 mL) was added in one portion at room temperature. Cesium carbonate (powder) (2445 g) was added in 3 portions over 30 minutes at a rate to maintain the internal temperature below 40° C. The reaction mixture was stirred for 15 hours at room temperature and monitored by TLC. The reaction mixture was filtered through a Celite® pad (1000 g) using a polypropylene filter pad and washed with ethyl acetate (3×2 L). The solids were discarded. Ethyl acetate (12 L) and aqueous saturated ammonium chloride solution (8 L) were added to the filtrate. The mixture was stirred vigorously for 15 minutes, and the layers were allowed to separate. The organic layer was collected, and the aqueous layer was extracted with ethyl acetate (3×6 L). The combined organic layers were washed with aqueous saturated ammonium chloride solution (2×8 L) and brine (10 L), dried using magnesium sulfate, filtered through a glass fiber filter, and the filtrate concentrated at 40-45° C. under vacuum to yield the product as viscous brown oil that contains residual ethyl acetate and DMF. Yield=3420 g (~100%, contains ethyl acetate and DMF), structure confirmed by $^1$H-NMR (CDCl$_3$).

Example 10

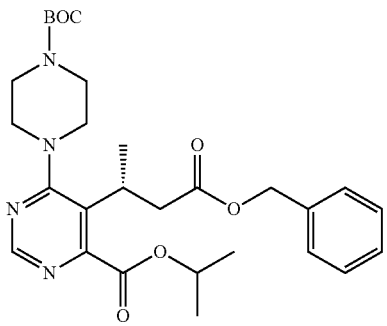 [SMILES: CC(C)OC(=O)c1ncnc(N2CCN(C(=O)OC(C)(C)C)CC2)c1[C@H](C)CC(=O)OCc1ccccc1]

(R)-isopropyl 5-(4-(benzyloxy)-4-oxobutan-2-yl)-6-(4-(tert-butoxycarbonyl)piperazin-1-yl)pyrimidine-4-carboxylate (R)-tert-butyl 4-(5-(4-(benzyloxy)-4-oxobutan-2-yl)-6-chloropyrimidin-4-yl)piperazine-1-carboxylate (1710 g) was dissolved in THF (4.0 L) and placed in a nitrogen-purged 5 gallon autoclave. Isopropanol (6.0 L) was added. The reaction mixture was sparged with nitrogen gas 5 times (25 psi), and the autoclave was heated to 35-40° C. A slurry of palladium acetate (81 g) and dppp (163 g) in isopropanol (2.0 L) was added at 40-45° C. and stirred. The reaction mixture was sparged with nitrogen gas 3 times (25 psi) and stirred for 20 minutes at 40-45° C. to dissolve the solids. A slurry of potassium carbonate, 325 mesh (299 g) in isopropanol (2.0 L) was added at 40-45° C. with stirring. The reaction mixture was sparged with nitrogen gas 5 times (25 psi), then sparged with carbon monoxide gas 5 times (40 psi). The autoclave was sparged with carbon monoxide gas to 55 psi. The reaction mixture was stirred at 50° C. and 55 psi (carbon monoxide gas) for a minimum of 50 hours and monitored by TLC and HPLC. The reaction mixture was cooled to room temperature and transferred into a filtration bottle. Silica gel (400 g) and Celite® (400 g) were added, and the reaction mixture was stirred open to air for 2 hours. The reaction mixture was filtered using a silica gel pad (1000 g) in a scintered funnel (D×H, 8×14 inches) and washed with ethyl acetate (4-5 L) and concentrated under vacuum to yield the product as viscous dark brown oil (contains residual dppp[O]$_2$. Yield=1900 g (~100%, contains residual dppp[O]$_2$), structure confirmed by $^1$H-NMR (CDCl$_3$).

Example 11

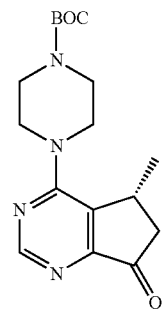

(R)-tert-butyl 4-(5-methyl-7-oxo-6,7-dihydro-5H-cyclopenta[d]pyrimidin-4-yl)piperazine-1-carboxylate A 3 L, 3-neck round bottom flask was equipped with a mechanical stirrer, drying tube, nitrogen inlet, thermocouple and cooling bath. The flask was charged with a solution of (R)-isopropyl 5-(4-(benzyloxy)-4-oxobutan-2-yl)-6-(4-(tert-butoxycarbonyl)piperazin-1-yl)pyrimidine-4-carboxylate, (110 g) in 2-methyl tetrahydrofuran (1.1 L) with stirring. The reaction mixture was cooled to 0° C. using a dry ice/acetone bath while sparging the reaction mixture subsurface with nitrogen gas for a minimum of 20 minutes. Under inert atmosphere, KOtBu (25.8 g) was added in two portions at 10 minutes intervals at a rate to maintain an internal temperature below 5° C. The reaction mixture was stirred for 20-30 minutes at 0 to 5° C. and monitored by TLC. The reaction mixture was cooled to an internal temperature of −5 to 0° C. Under inert atmosphere, formic acid (11.8 mL, 98%) was added via addition funnel over 5 minutes at a rate to maintain the internal temperature below 5° C. The pH was measured to be about 6 to 7. The (5R)-benzyl 4-(4-(tert-butoxycarbonyl)piperazin-1-yl)-5-methyl-7-oxo-6,7-dihydro-5H-cyclopenta[d]pyrimidine-6-carboxylate formed was used without isolation.

A separate vessel was charged with 10 wt % Pd/C [50% wet] (16.5 g) and 5% formic acid in 2-methyltetrahydrofuran (250 mL) under nitrogen. The reaction mixture was cooled to an internal temperature of −5 to 0° C. The Pd/C slurry was transferred to the reaction flask, and 2-methyltetrahydrofuran (250 mL) was used to rinse the container to transfer all of the Pd/C solids.

The reaction mixture was slowly warmed to 17-19° C., stirred at 18-19° C. for 0.5 to 1 hour, and monitored by TLC. The reaction was cooled to 15° C. and agitation was stopped and monitored by TLC. Aqueous saturated sodium bicarbonate solution (800 mL) was added slowly to quench the excess formic acid at a rate to maintain to minimize foaming. The reaction mixture was filtered through a Celite® pad on polypropylene (50 g) and the reaction flask was rinsed with 2-methyltetrahydrofuran (600 mL) and transferred as a wash of solids. Ethyl acetate (500 mL) was added to this filtrate and the layers were separated. The organic layer was washed with aqueous saturated sodium bicarbonate.solution (2×600 mL). The combined aqueous layers were washed with Ethyl acetate (1.0 L). The combined organic layers were washed with brine solution (1.0 L). Charcoal (50 g, 50 wt %) and magnesium sulfate (75 g, 75 wt %) were added to the organic layer and stirred for 5-10 minutes. The solids were removed via filtration, and the filtrate was concentrated at 40-45° C. under vacuum to yield the crude product as light brown semi-solid. Yield=50 g (crude), structure confirmed by $^1$H-NMR (CDCl$_3$).

Example 12

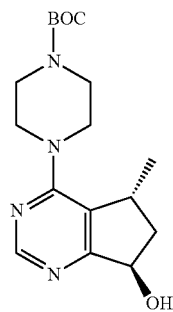

tert-butyl 4-4-((5R,7R)-7-hydroxy-5-methyl-6,7-dihydro-5H-cyclopenta[d]pyrimidin-4-yl)piperazine-1-carboxylate Example 12.1

Ru(MsDPEN)Cl Catalyzed Process

A 50 L, 3-necked round bottom flask was equipped with a thermocouple, mechanic stirrer, a nitrogen inlet and drying tube. To the flask was added (R)-tert-butyl 4-(5-methyl-7-oxo-6,7-dihydro-5H-cyclopenta[d]pyrimidin-4-yl)piperazine-1-carboxylate (1200 g), Ru(MsDPEN)Cl (MsDPEN is N-methanesulfonyl-1,2-diphenylethylenediamine). The mixture was stirred and the reaction surface was degassed with nitrogen for about 1 hr. Triethylamine (600 mL) was added in one portion. Formic acid (191 mL) was slowly added by the addition funnel over 15 mins. The reaction was stirred under slow nitrogen purge for about 15 h. The reaction mixture was concentrated under reduced pressure at about 40 to 45° C. to yield 1700 g crude product.

Example 12.2

RuCl(TsDACH) Catalyzed Process

A flask was equipped with a thermocouple, mechanic stirrer, a nitrogen inlet and drying tube. To the flask was added (R)-tert-butyl 4-(5-methyl-7-oxo-6,7-dihydro-5H-cyclopenta[d]pyrimidin-4-yl)piperazine-1-carboxylate (46.0 g, 139 mmol) followed by dichloromethane (1.10 L) and RuCl (TsDACH) catalyst (1.50 g, 2.80 mmol) with nitrogen degassing (gas dispersion tube) and agitation at room temperature. To the mixture was added triethylamine (23.0 mL, 167 mmol) with degassing. Formic acid (7.40 mL, 195 mmol) was slowly added to the mixture at a rate of about 1 mL/min. Good agitation with stirring was maintained until complete consumption of starting material (about 8-12 hr) as determined by HPLC analysis. The reaction was quenched with saturated sodium bicarbonate (2.00 vol., 100 mL), the layers were separated and the aqueous layer was discarded. The organic layer was washed with saturated sodium bicarbonate, saturated ammonium chloride and brine (2.00 vol., 100 mL each). The organics were dried over sodium sulfate, filtered and solvent exchanged into methanol.

The methanolic solution (5.00 vol.) of crude product was charged with 50 wt % SiliaBond® Thiol (Silicycle, Inc.) and 20 wt % Charcoal. The mixture was heated to about 50° C. and maintained at that temperature with good stirring overnight. The mixture was cooled to room temperature, filtered over a pad of Celite® and then polish filtered through a 0.45 micron filter. The mixture was distilled to a minimum working volume and concentrated under reduced pressure to afford the product (44.0 g, 95% yield), as a 96:4 mixture of trans/cis diastereomers) as solid. Trace amount of Ru metal was measured by ICP-EOS and found that the product contained less than about 20 ppm Ru. The product was purified by preparative HPLC under the following conditions or crystallization from ethyl acetate/heptane to yield 98.4% pure product, 97.7% de with about 100% ee.

All patents, patent applications, documents, and articles cited herein are herein incorporated by reference in their entireties.

The invention claimed is:
1. A process, comprising, contacting a compound of formula IV, or a salt thereof:

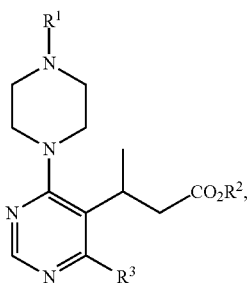

wherein
R¹ is hydrogen or an amino protecting group;
R² is hydrogen or optionally substituted $C_1$-$C_{12}$ alkyl; and
R³ is halogen,
with carbon monoxide, a carbonylation catalyst and an alcohol of formula R⁴OH to form a compound of formula III, or a salt thereof:

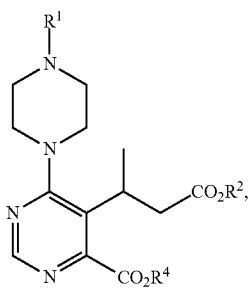

wherein
R⁴ is $C_1$-$C_6$ alkyl.

2. The process of claim 1, wherein the carbonylation catalyst comprises $Pd(OAc)_2$.

3. The process of claim 1, wherein R¹ is a Boc group.

4. The process of claim 1, wherein R² is methyl or benzyl.

5. The process of claim 1, wherein R³ is Cl.

6. The process of claim 1, wherein R⁴ is isopropyl.

7. The process of claim 1, further comprising (i) reacting the compound of formula III, or the salt thereof, with base to form an intermediate; and (ii) decarboxylating the intermediate to produce a compound of formula II or a salt thereof:

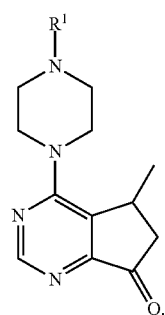

8. The process of claim 7, wherein the base comprises potassium t-butoxide.

9. The process of claim 7, wherein the decarboxylating further comprises a catalyst comprising Pd and hydrogen gas.

10. The process of claim 7, further comprising reducing the compound of formula II, or the salt thereof, to form a compound of formula I, or a salt thereof:

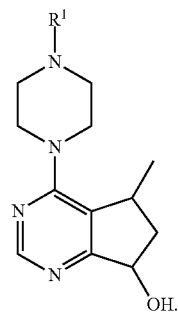

11. The process of claim 10, wherein the reducing comprises a catalyst comprising ruthenium and hydrogen gas.

12. The process of claim 1, wherein the compound of formula IV or the salt thereof is a compound of formula IVa:

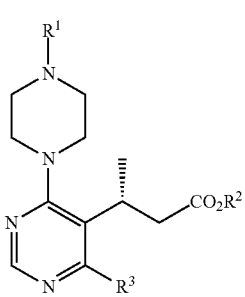

or a salt thereof, and the compound of formula III or the salt thereof is a compound of formula IIIa:

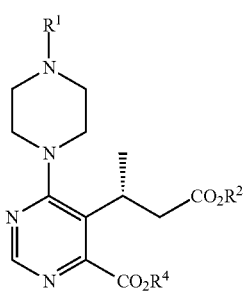

or a salt thereof.

13. The process of claim 12, further comprising preparing the compound of formula IVa or the salt thereof by contacting a corresponding of formula XIII or a salt thereof:

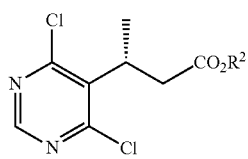

with a compound of formula

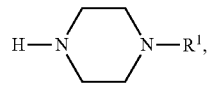

to form the compound of formula IVa or the salt thereof:

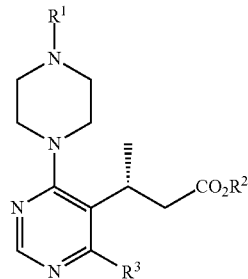

wherein $R^3$ is Cl.

14. The process of claim 13, further comprising preparing the compound of formula XIII or the salt thereof by chlorinating a corresponding compound of formula XII or a salt thereof:

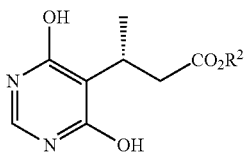

to form the compound of formula XIII or the salt thereof.

15. The process of claim 14, further comprising preparing the compound of formula XII or the salt thereof by reacting a compound of formula X or a salt thereof:

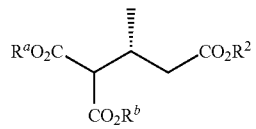

wherein $R^a$ and $R^b$ are independently $C_{1-12}$ alkyl, with formamidine to form the compound of formula XII or the salt thereof.

16. The process of claim 15, further comprising preparing the compound of formula X or the salt thereof by contacting a corresponding compound of formula XI:

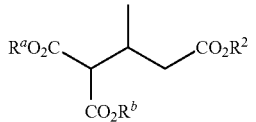

with a lipase to form the compound of formula X or the salt thereof.

* * * * *